United States Patent [19]

Bonacchi et al.

[11] Patent Number: 4,578,467

[45] Date of Patent: Mar. 25, 1986

[54] PROCESS FOR THE PREPARATION OF 1-PYRIDYL-ALKYL-4-ARYL PIPERAZINES WHICH ARE USEFUL AS ANTIHYPERTENSIVE COMPOUNDS, THEIR SEPARATION INTO THE RESPECTIVE OPTICAL ANTIPODES, AND THE STEREOISOMERIC COMPOUNDS SO OBTAINED

[75] Inventors: Graziano Bonacchi; Mauro Fedi; Mario Giannini, all of Florence, Italy

[73] Assignee: Malesci S.p.A. Instituto Farmacobiologico, Florence, Italy

[21] Appl. No.: 627,583

[22] Filed: Jul. 3, 1984

[30] Foreign Application Priority Data

Jul. 11, 1983 [IT] Italy .................. 48664 A/83

[51] Int. Cl.⁴ .................. C07D 401/06; C07D 401/12; A61K 31/495
[52] U.S. Cl. .................. 544/360; 514/252
[58] Field of Search .................. 544/360

[56] References Cited

U.S. PATENT DOCUMENTS 3,332,949  7/1967  Kirchner .................. 544/360
3,448,192  6/1969  Mauvernay .................. 544/360

OTHER PUBLICATIONS

Corey, E. J., et al, J.A.C.S., 87, 1353–1364, (1965).
Bacciarelli, C., et al, Chemical Abstract 94:185385m, (1981).
Derwent Abstract, 12797w/08.

Primary Examiner—George F. Lesmes
Assistant Examiner—S. A. Gibson
Attorney, Agent, or Firm—Beveridge, DeGrandi & Weilacher

[57] ABSTRACT

A process for the preparation of 1-pyridyl-alkyl-4-aryl piperazines, in the racemic form, of the formula

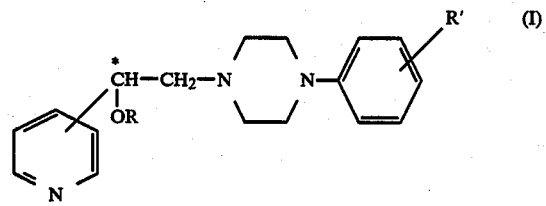

in which:
the pyridine ring is alpha-, beta-, or gamma-substituted;
$R=H$; $C_nH_{2n+1}$, n being in the range from 1 to 4;
$R'=H$, halogen, $CH_3$, $OCH_3$, in which process:
(a) pyridine aldehyde is reacted between $-5°$ C. and $0°$ C. with $(CH_3)_2S=CH_2$;
(b) the oxirane so obtained is treated with an arylpiperazine;
(c) the hydroxyl derivative obtained in (b), after salification with alkaline hydrides or hydrates in a solvent medium is treated with alkylating agents, and the separation of the compounds so obtained into the respective optical antipodes.

8 Claims, No Drawings

PROCESS FOR THE PREPARATION OF 1-PYRIDYL-ALKYL-4-ARYL PIPERAZINES WHICH ARE USEFUL AS ANTIHYPERTENSIVE COMPOUNDS, THEIR SEPARATION INTO THE RESPECTIVE OPTICAL ANTIPODES, AND THE STEREOISOMERIC COMPOUNDS SO OBTAINED

DISCLOSURE OF THE INVENTION

This invention relates to a process for the preparation of 1-pyridyl-alkyl-4-aryl piperazines, useful for their anti-hypertensive activity, their separation into the respective optical antipodes and the stereoisomeric compounds so obtained. More particularly, the present invention is concerned with a fundamental process for the preparation of racemic derivatives of the 1-pyriyl-alkyl-4-aryl piperazine corresponding to the general formula:

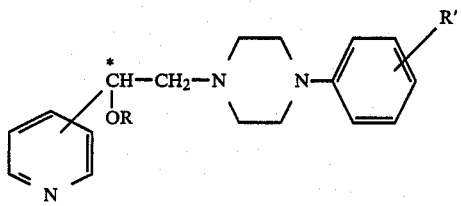

wherein:
the pyridine ring is alpha-, beta- or gamma-substituted;
R=H, $C_nH_{2n+1}$, n being in the range from 1 to 4;
R'=H, Halogen, $CH_3$, $OCH_3$;
such derivatives being useful for their anti-hypertensive activity, which can be ascribed to their vasodilating and/or alpha-adrenergic receptors blocking properties (M. Giannini, Italian Patent No. 1056055; C. Bacciarelli and co-workers, Boll. Chim. Farm., 119, 608; 1980) as well as of their stereoisomeric forms, obtained by separation, which show similar activities. More exactly, such stereoisomeric forms show remarkably different hypotensive activities from form to form as well as with respect to the racemic form.

It is to be observed that the compounds corresponding to the general formula (I) are already known in the state of the art, which suggests for the preparation of the same a multi-stage process (flowsheet A) which process is claimed in the Italian patent cited above and consists of the following steps:

(1) the reaction of bromoacetylpyridine bromhydrate with arylpiperazine under a nitrogen blanket in methyl alcohol and in the presence of triethylamine;
(2) the reduction of ketonic compound obtained in step (1) to the alcohol compound with $NaBH_4$ in a hydroalcoholic solution;
(3) the chlorination of the alcohol obtained in step (2) with $SOCl_2$ in $CHCl_3$;
(4) the addition of the resulting chloroderivative obtained in step (3) to the alcoholic solution of the sodium alcoholate, and the final isolation of the desired ether compounds.

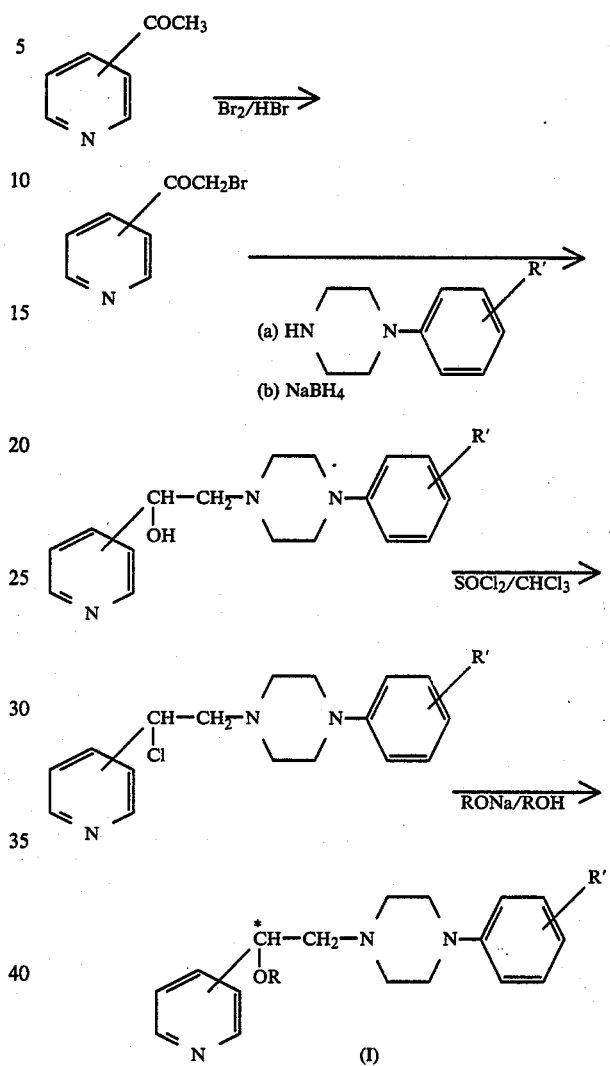

FLOWSHEET A

It is a specific object of the present invention a process for the preparation of 1-pyridyl-alkyl-4-aryl piperazines corresponding to the general formula:

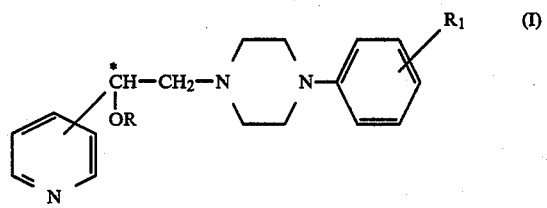

The pyridine ring is alpha-, beta- or gamma-substituted;
R=H, $C_nH_{2n+1}$, n being in the range from 1 to 4;
R'=H, halogen, $CH_3$, $OCH_3$;
said process being characterized in that:
(a) pyridine aldehyde is reacted between $-5°$ C. and $0°$ C. with $(CH_3)_2S=CH_2$;
(b) the oxirane so obtained is treated with an arylpiperazine;
(c) the hydroxyl derivative obtained in step (b), after salification with alkaline hydrides or hydrates in a solvent medium, is treated with alkylating agents; according to the flowsheet B.

Preferably the step (a) is carried out under a nitrogen blanket and within a mixture of dimethylsulfoxide and tetrahydrofurane, and the reactive is obtained in situ from trimethylsulfonium iodide and sodium hydride (E. J. Corey and M. Chaykowsky: J. Am. Chem. Soc. 87, 1353, 1965).

Thus in addition in the step (b) the oxirane compound is preferably refluxed in ethyl alcohol, in isopropyl alcohol, in propyl alcohol, in butyl alcohol or in dioxane.

In step (c) the etherification is carried out by previous salification, preferably with sodium hydride or with alkaline hydrates, followed by a treatment with dialkylsulfates or alkylhalides, employing dimethylsulfoxide or dimethylformamide and making the reaction to proceed at room temperature.

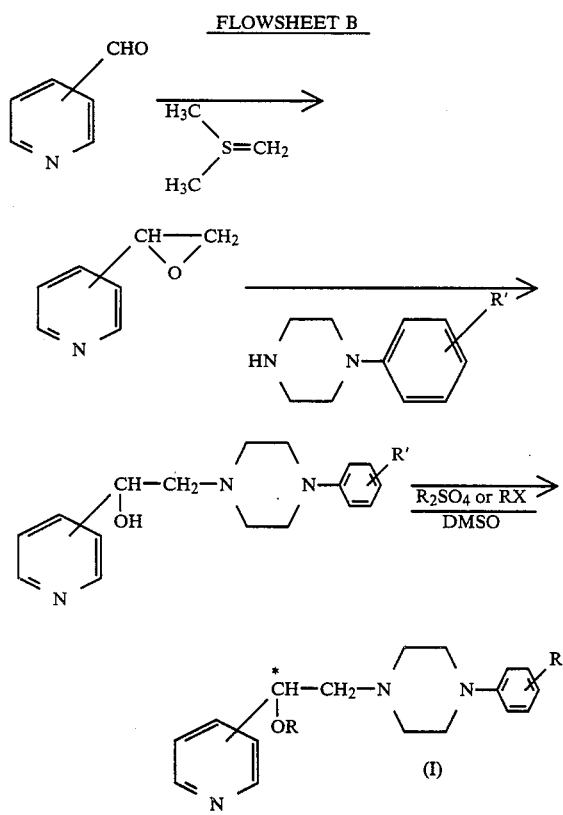

FLOWSHEET B

It is to be put into evidence that, according to the process of the present invention, the following advantages are obtained:

(1) an easy recovery of the arylpiperazines, which are costly compounds, that have not reacted in the preparation of the hydroxyl derivative, the latter being obtained with a 50% yield, which is equivalent to the yield obtained following the process of the previous art;

(2) an easy etherification in a single step, with a 70% yield, that is a yield remarkably higher than the yield obtained following the prior art process which included in addition a very difficult step passing through the chloroderivative compound (flowsheet A).

The compounds thus obtained possess an asymmetric carbon atom, marked with an asterisk in the general formula (I) so that they exist in two stereoisomeric forms which can be obtained separately, in case of R=H, by a process which exploits the possibility of preparing a mixture of diastereoisomeric esters which are separated successively and finally hydrolyzed.

It is now well known that very often the activity of the racemic compounds can be predominantly or exclusively ascribed to one only of the optical isomers (P. N. Patil and co-workers, Pharm. Rev. 26, 323–392; 1975), so that in such cases it is useful and prudential to use the only enantiomer which is more active clinically.

Though the compounds showing alpha blocking activity, except for the class of the benzodioxanes, have no stereoselectivity in general (P.B.M.W.M. Timmermans; TIPS 285; 1983) it has been found that the dextrorotatory isomer of the compound corresponding to the formula I with $R=C_2H_5$ and $R_1=O—OCH_3$ is remarkably endowed with a higher anti-hypertensive activity than the racemic compound while concerning the same toxicity of said racemic compound, whereas the laevorotatory isomer is almost inactive.

It follows from the above that, employing the dextrorotatory isomer, lower doses are possible than those for the racemic form in order to obtain the same therapeutic effects with less toxic effects as a whole.

In order to make clearer the advantages obtainable by employing pharmaceutical compositions containing the dextrorotatory isomer as the active agent, reference is had below to the data concerning the toxicity, the blocking activity in vitro and the hypotensive activity in vivo as relative to the racemic compound (r) and to the dextrorotatory (+) and laevorotatory (−) isomers.

Acute toxicity

Male Swiss mice of 20–25 g body weight were treated by i.p. injection with rated concentrations of the three compounds. The values of $DL_{50}$ and the relative confidence limits were calculated according to the method of Wilcoxon (J. Pharm. Exp. Ther. 96, 99; 1949).

$DL_{50}$ mg/kg (95% confidence limits)

| (r) | 75 | (72–77) |
| (+) | 65 | (58–72) |
| (−) | 68 | (64–72) |

No significative differences were shown either in the $LD_{50}$ values or in the symptomatology.

Alpha-blocking attivities in vitro

The aorta isolated from a rabbit and prepared according to the procedure of Furchgott and Bhadrakom (J. Pharm. Exp. Ther. 108, 129; 1953) was tested with cumulative doses of nor-adrenaline till maximum responde obtainable in the absence and in the presence of the three compounds. The $pA_2$ values were calculated according to Ariens and Van Rossum (Arch. Int. Pharmacodyn. 110, 275; 1957)

| (r) | 8.62 ± 0.11 |
| (+) | 9.04 ± 0.03 |
| (−) | 6.95 ± 0.05 |

It is evident from the Table given above that the (+) derivative is 100 times as active as the (−) derivative and almost 3 times as active as the (r) compound in blocking the post-synaptic alpha-receptors response to nor-adrenaline.

Hypotensive activity in vivo

Spontaneously hypertensive rats were employed after they were fasted for 16 hours and tested for their systemic pressure by bloodless measurements before and after oral administration of the three compounds at the doses of 5-10-15 mg/kg.

The administration of all the compounds gives rise to a lowering of the dose-dependent hypertension, because the regression coefficients are always significative. The $ED_{50}$ values in mg/kg, obtained from the graphs of the activities observed, are as follows:

|     | 30'    | 1h, 30' |
| --- | ------ | ------- |
| (r) | 7.8    | 18.8    |
| (+) | 5.5    | 10.9    |
| (−) | (35.9) | (74.9)  |

The data concerning the laevorotatory isomer were obtained by extrapolation so that they have a merely indicative meaning.

It is evident from the above that also in cases of the in vivo experiments the most active form was the dextrorotatory (+) one whereas the laevorotatory (−) form shows a quite low activity.

According to the teachings of the present invention, the separation of the optical antipodes of the compound of the formula

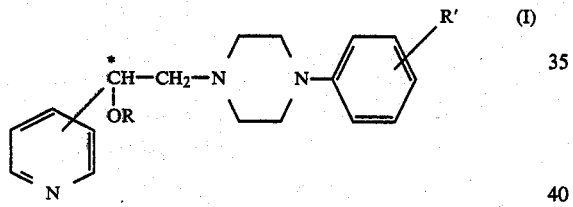

(I)

in which:
the pyridine ring is alpha-, beta- or gamma-substituted;
$R = H, C_nH_{2n+1}$, wherein n is in the range from 1 to 4;
$R' = H$, halogen, $CH_3$, $OCH_3$, is carried out following a process which is typical of the present invention and it is characterized in that (flowsheet C):
(a) the racemic alcoholic derivative of the formula (±II)

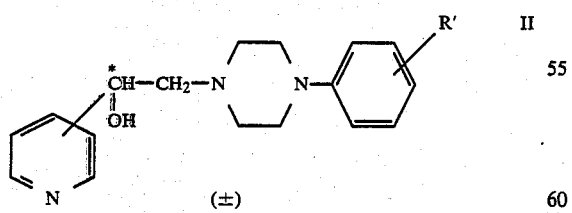

II (±)

is reacted with the chloride of the optically active acetylmandelic acid;
(b) the diastereoisomeric compound obtained is hydrolyzed with a hydroalcoholic KOH solution at room temperature;
(c) the optically active alcoholic derivative so obtained, after salification with alkaline hydrides or hydrates in a solvent medium, is treated with alkylating agents.

Preferably the step (a) is carried out in a chloroformic solution at room temperature.

Similarly the diastereoisomeric esters of the formula III, before being hydrolyzed with hydroalcoholic KOH at room temperature, are preferably purified by fractional crystallization froma isopropyl alcohol and then from methyl alcohol.

It is to be remarked that step (c) above allows the transformation of the (+)II and correspondingly of the (−) II compounds into the respective optically active esters with no racemization.

FLOWSHEET C

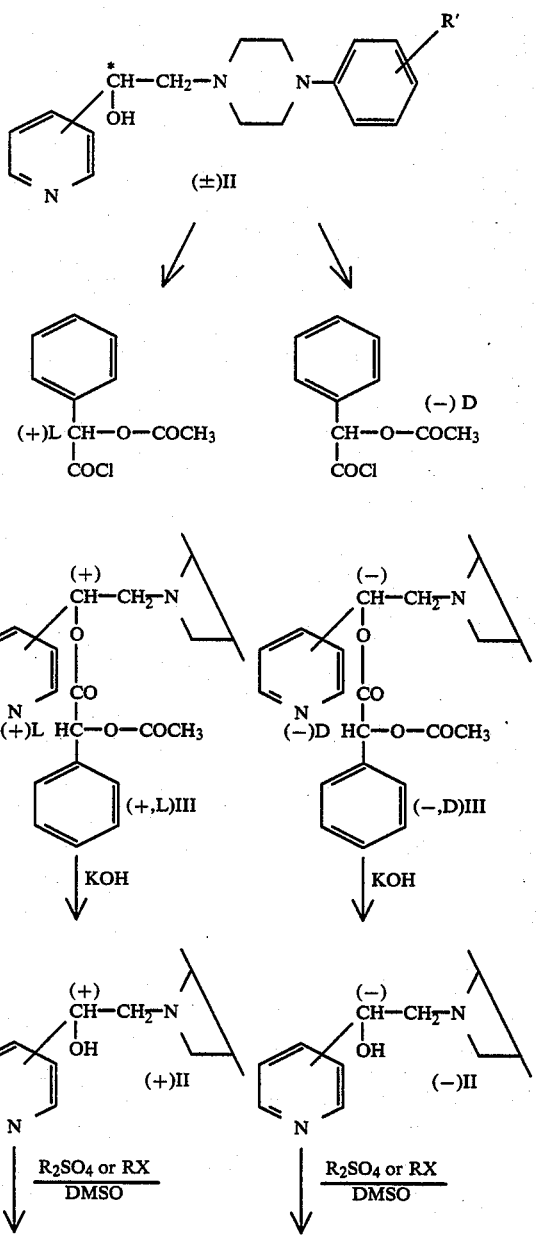

-continued
FLOWSHEET C

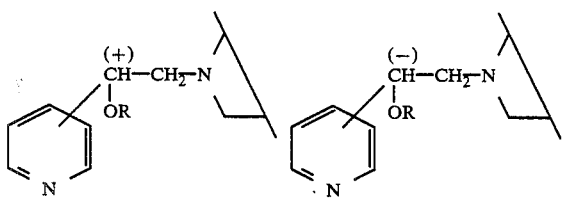

wherein:

R′=H, halogen, OCH₃, CH₃;

R=$C_nH_{2n+1}$, n being in the range of from 1 to 4.

The examples given in the following are for the purpose of better illustrating the present invention without limiting the same.

EXAMPLE 1

The preparation of (±) 1-(2-hydroxy-2-(3′-pyridyl)-ethyl)-4 (o-methoxyphenyl) piperazine.

This compound corresponds to the general formula (I) in which R=H, R′=o—OCH₃.

85 ml of dimethylsulfoxide is added to 9.6 g (0.2 moles) of NaH 50% in oil, previously washed with hexane and vacuum dried, the addition being carried out with stirring and under a nitrogen blanket. The mixture is stirred at 65° C. for 1 hour, and 85 ml of anhydrous tetrahydrofurane is added to the solution so obtained, at room temperature. After cooling with salt and ice down to −10° C., 40.75 g (0.2 moles) of trimethylsulfonium iodide dissolved in 145 ml of dimethylsulfoxide is added portionwise. During the addition the temperature must be kept below 0° C. The solution is kept for 10 minutes under stirring at −5° C. and 10.7 g (0.1 moles) of pyridine 3-aldehyde dissolved in 16 ml of dimethylsulfoxide is added continuously in about 10 minutes.

After 20 minutes the ice and salt bath is removed, and the temperature is allowed to rise to the room temperature, then the solution is warmed to 30°-35° C. for 1 hour. After a further hour at room temperature, the mixture is treated with 1 liter of water and it is immediately extracted for three times with a whole volume of 600 ml of methylene chloride. From the organic extracts, after washing the same many times with water and drying with Na₂SO₄ and concentrating them to dryness under vacuum, the oxirane compound is obtained with high yield (higher than 75%) in the form of a not very dense oil which, after a positive NMR check, is dissolved in 200 ml of isopropyl alcohol and treated with 23 g (0.12 moles) od o-methoxyphenyl piperazine. The solution obtained is kept under reflux for 15 hours, then it is concentrated to dryness, the oily residue is dissolved in diluted HCl till pH 4.5-5, then it is extracted with ether and the aqueous solution is slowly alkalized with diluted NH₄OH till pH 10.

Thus, 17 g is obtained of the desired product, which is already sufficiently pure (t.l.c.: silica gel; eluent mixture; cyclohexane, ethyl alcohol, triethylamine in the ratio 6/1/1), melting point 72°-74° C. (from ligroin), yield 50%.

From the mother liquors it is possible to recover, after further alkalinization with concentrated NaOH and chloroform extraction, a large part of the unreacted o-methoxyphenyl piperazine, together with a further 10% of the desired product.

EXAMPLE 2

The preparation of (±) 1-(2-ethoxy-2-(3′-pyridyl)-ethyl)-4-(o-methoxyphenyl) piperazine.

This compound corresponds to the general formula (I) where R=C₂H₅; R′=o-OCH₃.

90 ml of dimethylsulfoxide is added with stirring to 5.3 g (0.11 moles) of 50% NaH in oil, which was previously washed with hexane and vacuum dried. After about 15 minutes 31.3 g (0.1 moles) of (±) 1-(2-hydroxy-2-(3′-pyridyl)ethyl)-4-(o-methoxyphenyl)-piperazine dried under high vacuum is added portionwise during 1.5 hours, this time being necessary in order to keep the temperature between 25° and 32° C. and to avoid an excessive gas evolution.

When the addition is over, the mixture is kept under stirring for 40 minutes at room temperature, then 16.2 g (0.105 moles) of diethylsulfate is added with caution, cooling ice and water to keep the temperature below 30° C. After keeping the solution standing overnight, it is poured into 200 ml of water, then the mixture is kept 10 minutes under stirring and it is then extracted for three times with 500 ml of ether.

The ether extracts are washed three times with water, dried with Na₂SO₄ and concentrated to dryness.

The oily residue is distilled under high vacuum: boiling point 190° C. at 0.2 mm Hg; yield 23.9 g, 70%.

The mono-hydrochloride is obtained dissolving the oil in isopropyl alcohol and adding one equivalent of gaseous HCl dissolved in alcohol. Thus a white microcrystalline product is precipitated, with a melting point of 181° C. (from isopropyl alcohol).

EXAMPLE 3

The preparation of (±) 1-(2-hydroxy-2-(3′-pyridyl)-ethyl)-4-(o-methoxyphenyl) piperazine 23.3 g (0.11 moles) of the chloride of the L (+) acetyl mandelic acid dissolved in 100 ml of CHCl₃ is added dropwise and stirring to 31.3 g (0.1 moles) of (±) 1-(2-hydroxy-2-(3′-pyridyl)ethyl)-4-(o-methoxyphenyl) piperazine dried under vacuum and dissolved in 300 ml of alcohol-free CHCl₃.

The solution, which darkens rapidly, is left at room temperature overnight; then it is concentrated under vacuum till dryness and the dense oily residue slowly solidifies by rubbing with ether.

The solid so obtained is filtered, high vacuum dried at 50°-60° C. for 1 hour, then it is dissolved in 930 ml of isopropyl alcohol previously heated up to 60°-70° C.

The solution is pooled with ice and water, and the crystalline precipitate which rapidly begins to form is filtered after 1 hour.

Melting point 194°-196° C.; yield 11 g (41%).

$|\alpha|_D = +72.1°$ (c=1.39 in MeOH).

The mono-hydrochloride of the diastereoisomeric ester (+L), successively recrystallized from MeOH (1 g/3 ml) shows the following final characteristics:

melting point 196°-198° C.; $[\alpha]_D = +76.1°$ (c=1.379 in MeOH)

empirical formula: C₂₈H₃₂ClN₃O₅; molecular weight 526.04; elements analyzed: C, H, N; analyses performed by NMR and IR.

To a solution of 8 g (15.2 mmoles) of of the ester in 160 ml of MeOH, 1.16 g (20.7 mmoles) is added of KOH dissolved in 22 ml of H₂O. The solution, after standing overnight, is concentrated under vacuum till dryness and the residue after solubilization in diluted hydrochloric acid, is extracted with ether many times. From the aqueous solution after alkalinization with diluted NH₄OH, 3.9 g (78%) of the (+) enantiomer are precipitated.

$[\alpha]_D = +42.5°$ (c=1.53 in 1N HCl) cl EXAMPLE 4

The preparation of (−)1-(2-hydroxy-2-(3'-pyridyl)-ethyl)-4-(o-methoxyphenyl) piperazine This preparation is carried out by reacting with the chloride of the D (−) acetylmandelic acid the (±) 1-(2-hydroxy-2-(3'-pyridyl)-ethyl)-4-(o-methoxyphenyl) piperazine enriched in the laevorotatory form as it is obtained by the saponification of the ester recovered from the isopropanol mother waters of the crystallization described in example 2.

The reaction conditions are identical with those given in the preceding example.

The diastereoisomeric ester (−,D) shows the following features:

melting point 191°–194° C.; $[\alpha]_D = -71.7°$ (c=1.394 in MeOH).

The enantiomeric (−) compound shows:
$[\alpha]_D = -44.8°$ (c=1.45 in 1N HCl).

EXAMPLE 5

The preparation of (+) 1-(2-ethoxy-2-(3'-pyridyl)-ethyl)-4-(o-methoxyphenyl) piperazine The present preparation is carried out according to the method described in example 2, starting from the enantiomeric hydroxyl derivative (+) I.

The oily product so obtained shows $[\alpha]_D = +70.1°$ (c=1.568 in 1N HCl).

EXAMPLE 6

The preparation of (−) 1-(2-ethoxy-2-(3'-pyridyl)-ethyl)-4-(o-methoxyphenyl) piperazine The present preparation is carried out according to the method described in example 2, starting from the enantiomeric hydroxyl derivative (−).

The oily product so obtained shows $[\alpha]_D = -71.9°$ (c=1.53 in 1N HCl).

The present invention has been described with reference to some of its specific embodiments, but it is to be understood that modifications and changes can be introduced in the same without going out of the spirit and the scope of the invention for which the priority rights are claimed.

We claim:

1. A process for the preparation of compounds of the general formula

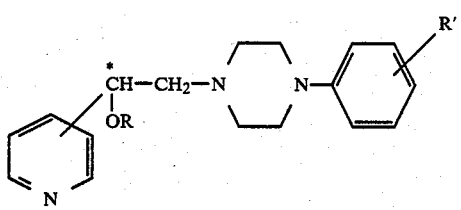

wherein:
the pyridine ring is alpha-, beta- or gamma-substituted;
R=H; $C_nH_{2n+1}$, n being in the range from 1 to 4;
R'=H, halogen, CH₃, OCH₃;
which process is characterized in that:
(a) pyridine aldehyde is reacted at a temperature from −5° to 0° C. with (CH₃)₂S═CH₂;
(b) the oxirane so obtained is treated with an aryl piperazine;
(c) the hydroxyl derivative obtained in step (b), after salification with alkaline hydrides or hydrates in a solvent medium, is treated with alkylating agents, according to the following flowsheet:

FLOWSHEET B

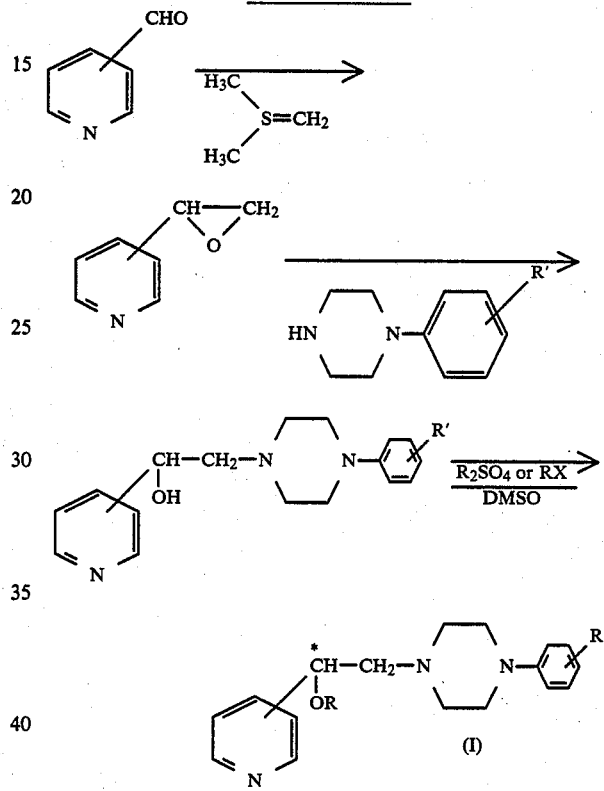

2. A process according to claim 1, wherein the step (a) is carried out under a nitrogen blanket and in a mixture of dimethylsulfoxide and tetrahydrofurane.

3. A process according to claim 1, wherein the step (b) is carried out with a long boiling operation in isopropyl alcohol.

4. A process according to claim 1 wherein the step (b) is carried out by a long boiling operation in ethyl alcohol, propyl alcohol, butyl alcohol or in dioxane.

5. A process according to claim 1, wherein, in the step (c), the salification is carried out with sodium hydride in dimethylsulfoxide or in dimethyl formamide.

6. A process according to claim 1 wherein, in the step (c), the salification is carried out with potassium hydrate in dimethylsulfoxide.

7. A process according to claim 1 wherein, in the step (c), tha alkylating agents are the alkylsulfates.

8. A process according to claim 1, wherein in the step (c), the alkylating agents are alkyl halides.

* * * * *